United States Patent
Bagga et al.

(10) Patent No.: US 6,821,280 B1
(45) Date of Patent: Nov. 23, 2004

(54) DISTRACTING AND CURETTING INSTRUMENT

(76) Inventors: Charanpreet S. Bagga, 1083 King Rd., Apt. He111, Malvern, PA (US) 19355; Eric Gray, 5720 Linda La., Rockford, MN (US) 55373; John E. Regan, 147 S Carmelina, Brentwood, CA (US) 90049

( * ) Notice: Subject to any disclaimer, the term of this patent is extended or adjusted under 35 U.S.C. 154(b) by 222 days.

(21) Appl. No.: 09/631,502

(22) Filed: Aug. 3, 2000

(51) Int. Cl.[7] .............................................. A61B 17/02
(52) U.S. Cl. ............................................ 606/80; 606/61
(58) Field of Search ............................ 606/79, 80, 82, 606/90, 61, 167, 170, 179, 160, 84, 131, 159, 161, 162, 166

(56) References Cited

U.S. PATENT DOCUMENTS

| | | | |
|---|---|---|---|
| 817,042 A | 4/1906 | Burns | |
| 3,848,601 A | 11/1974 | Ma et al. | |
| 3,937,222 A | * 2/1976 | Banko ......................... | 606/107 |
| 4,867,157 A | * 9/1989 | McGurk-Burleson et al. ........................... | 606/170 |
| 4,878,915 A | 11/1989 | Brantigan | |
| 4,961,740 A | 10/1990 | Ray et al. | |
| 5,015,247 A | 5/1991 | Michelson | |
| 5,026,373 A | 6/1991 | Ray et al. | |
| 5,122,134 A | * 6/1992 | Borzone et al. ............ | 606/170 |
| 5,484,437 A | 1/1996 | Michelson | |
| 5,489,307 A | 2/1996 | Kuslich et al. | |
| 5,505,732 A | 4/1996 | Michelson | |
| 5,571,109 A | 11/1996 | Bertagnoli | |
| 5,685,673 A | * 11/1997 | Jarvis .......................... | 606/180 |
| 5,722,977 A | 3/1998 | Wilhelmy | |
| 5,741,253 A | 4/1998 | Michelson | |
| 5,772,661 A | 6/1998 | Michelson | |
| 5,797,909 A | 8/1998 | Michelson | |
| 5,865,847 A | 2/1999 | Kohrs et al. | |
| 5,885,299 A | 3/1999 | Winslow et al. | |
| 5,906,616 A | 5/1999 | Pavlov et al. | |
| 5,928,242 A | 7/1999 | Kuslich et al. | |
| 5,947,971 A | 9/1999 | Kuslich et al. | |
| 6,245,084 B1 | * 6/2001 | Mark et al. ................. | 606/170 |

FOREIGN PATENT DOCUMENTS

| | | |
|---|---|---|
| DE | 3800482 A1 | 7/1980 |
| EP | 0 646 366 A1 | 4/1995 |
| EP | 0 796 593 A2 | 9/1997 |
| WO | WO 91/06261 | 5/1991 |
| WO | WO 96/22747 | 8/1996 |
| WO | WO 97/33525 | 9/1997 |
| WO | WO 98/17208 | 4/1998 |

OTHER PUBLICATIONS

Brochure, AcroMed Spine Tools, PLIG Instruments, "Restore disc space height and prepare endplates for fusion graft".

Brochure, "Surgical Technique Using Bone Dowel Instrumentation", *Sofamor Danek, The Spine Specialist*, 20 pgs. date unknown.

* cited by examiner

*Primary Examiner*—David O. Reip
*Assistant Examiner*—Jessica R. Baxter
(74) *Attorney, Agent, or Firm*—Faegre & Benson LLP

(57) ABSTRACT

An instrument for cutting and/or curetting during surgery is disclosed. The instruments of the invention are particularly advantageous for use in removing disc material from an intervertebral disc space. In a preferred embodiment, rotation of the instrument around a longitudinal axis of the instrument provides for intermittently distracting vertebrae adjacent to the intervertebral disc space during rotation.

22 Claims, 2 Drawing Sheets

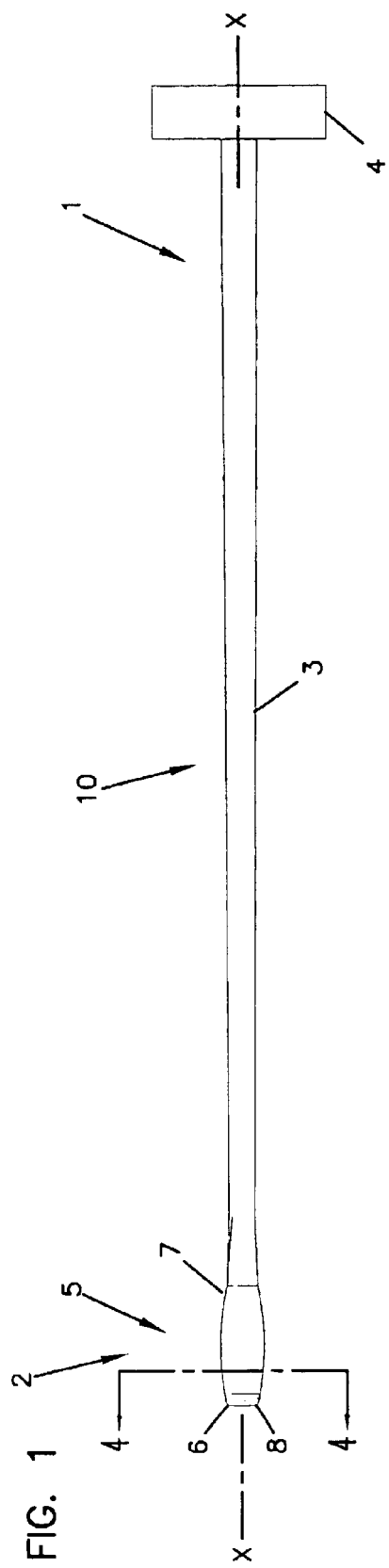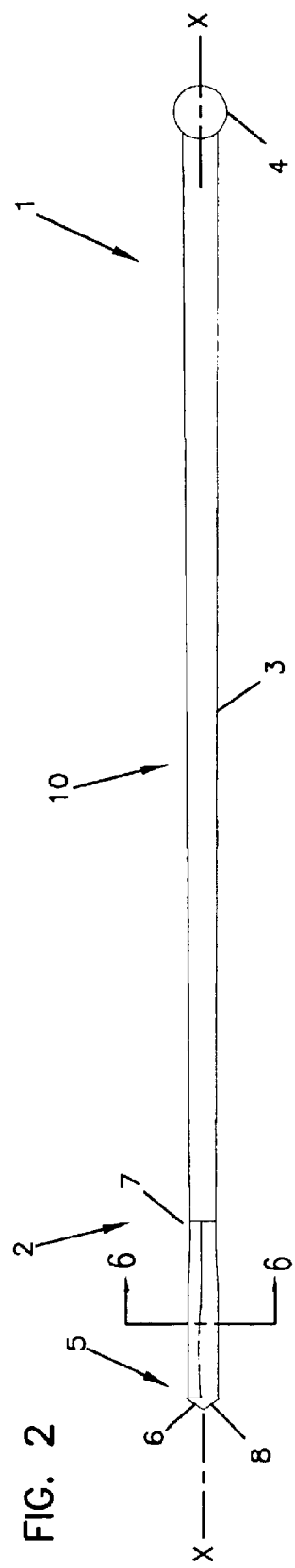

DISTRACTING AND CURETTING INSTRUMENT

FIELD OF THE INVENTION

The present invention is directed to surgical devices and procedures. In particular, the invention provides instruments for curetting, bone distracting and removing tissue from a surgical site. In one embodiment, the invention is particularly advantageous for removing disc material from an intervertebral disc space.

BACKGROUND OF THE INVENTION

Surgical instruments and techniques are known for performing procedures at and around vertebral bodies, including the intervertebral disc space. Such techniques include, for example, intervertebral disc decompression, vertebral fusion, etc. Often times such procedures include removing some or all of the disc material between vertebrae. Many known systems for removing disc material require multiple instruments or multiple steps for cutting the material to be removed, curetting the surfaces surrounding the disc material and removing the cut or curetted material from the disc space. The need for multiple instruments or multiple steps reduces surgical efficiency and can increase the overall time spent performing the procedure.

Accordingly, there is a continuing need for instrumentation and methods which reduce the time and steps needed to perform cutting, curetting and/or removal procedures in surgery. The present invention is directed to addressing this need.

SUMMARY OF THE INVENTION

The present invention provides instrumentation and methods for cutting, curetting and/or removing material from a surgical site. The invention also provides for distracting vertebrae that are adjacent an intervertebral disc space.

In one embodiment, the invention provides a surgical instrument having a proximal end spaced apart from a distal end along a shaft having a longitudinal axis passing therethrough. At the proximal end, the instrument includes a handle for operating the device. At the distal end, the instrument includes a working head including a blade for cutting, a distracting dimension for distracting and, in some embodiments, a collecting element to collect cut material and facilitate removal of the cut material from the surgical site.

In a typical embodiment the blade of the working head includes a leading and a trailing end and has a serpentinoid or "S" shaped configuration. A first cutting surface extends along a first edge from the leading end to the trailing end of the blade and a second cutting surface extends from the leading end to the trailing end along a second edge of the blade. If present, the collecting element is arranged to overlie some or all of the serpentinoid configuration at the leading end of the head. In addition, the working head can have a height dimension, width dimension and a diagonal dimension such that the diagonal dimension is greater than the height dimension which is greater than the width dimension.

In use, rotation of the working head of the instrument around a longitudinal axis in a first direction provides for cutting and/or curetting materials surrounding the blade. The cutting surfaces are configured and arranged in such a manner that when rotated in an opposite direction the cutting edges are not oriented for cutting material surrounding the blade. In addition, when positioned in an intervertebral disc space having a disc height less than the diagonal dimension of the working head, rotation of the instrument provides for distraction of the vertebrae adjacent to the disc space when the diagonal dimension of the blade is oriented at or near parallel with the longitudinal axis of the spinal column. The instruments of the invention can be particularly advantageous for use in cutting and/or curetting material from an intervertebral disc space.

BRIEF DESCRIPTION OF THE DRAWINGS

FIG. 1 is a side view of a preferred embodiment of a surgical instrument according to the invention;

FIG. 2 is a side view of the surgical instrument of FIG. 1 rotated 90 degrees around axis X—X;

DETAILED DESCRIPTION

Figure 4:
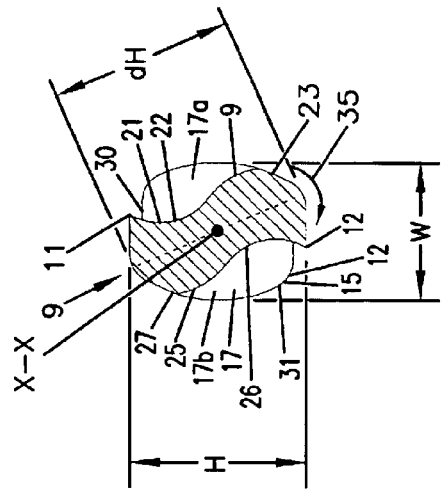
FIG. 4 is a transverse cross-section through line 4—4 of the surgical instrument of FIG. 1.

The invention is directed to surgical instruments for cutting, curetting and/or removing material from a surgical site. The instruments include a proximal end and distal end spaced apart along a shaft. A longitudinal axis X—X passes through the instruments from the proximal end to the distal end. A working head is present at the distal end and a handle for operating the instrument at the proximal end. A blade for cutting and curetting is located on the working head. The working head can also provide for distraction of vertebrae adjacent an intervertebral disc space. In some embodiments, the working head can also include a collecting element to facilitate removal of material from the surgical site.

In a preferred embodiment, the working head of the instrument includes a width dimension which is less than a height dimension which is less than a diagonal dimension. According to this embodiment, when the instrument is rotated around the longitudinal axis such that the diagonal dimension is oriented parallel to the long axis of the vertebral column, the vertebrae can be distracted and will be spaced apart from each other by a distance determined by the diagonal dimension of the working head.

Throughout the present description guidance may be provided through lists of examples. In each instance, the recited list serves only as a representative group. It is not meant, however, that the list is exclusive.

Unless otherwise stated, the terms "proximal" and "distal" are relative terms, the term "proximal" referring to a location nearest the operator of the disclosed instruments and the term "distal" referring to a location farthest from the operator. Thus, generally, when using an instrument of the invention for cutting and removing material from an intervertebral disc space through an anterior approach, the instrument is advanced from the anterior surface of the vertebral body (proximal) towards the posterior surface (distal) of the vertebral body. Likewise, in a posterior approach, the instrument is advanced from the posterior surface "proximal" toward the anterior surface "distal" of the vertebral body. Similar relative orientations also apply for lateral approaches to the vertebrae.

The "height" of the disc space is the dimension from the end plate of a superior vertebrae to the end plate of an inferior vertebrae adjacent to the disc space.

The height, width and diagonal dimension of the working head of an instrument of the invention can vary. Kits will be available including multiple instruments of the invention each having incrementally sized height, width and diagonal dimensions suitable for use in a particular surgical area for a particular surgical procedure.

DETAILED DESCRIPTION OF THE ILLUSTRATED EMBODIMENT

The invention will be described with reference to the accompanying drawings. The illustrated embodiment and description are for exemplary purposes to facilitate comprehension of the invention and should not be construed to limit the scope of the invention.

FIG. 1 is a side view of one embodiment of a surgical instrument 10 according to the invention. As illustrated, surgical instrument 10 has a proximal end 1 and a distal end 2 spaced along a longitudinal shaft 3. The proximal end 1 of surgical instrument 10 includes a handle 4 for rotating surgical instrument 10 around longitudinal axis X—X passing through shaft 3. At distal end 2, surgical instrument 10 includes a working head 5 having a leading end 6 and trailing end 7. Leading end 6 includes a tapered leading surface 8 at the leading end 6 of working head 5.

Figure 3:
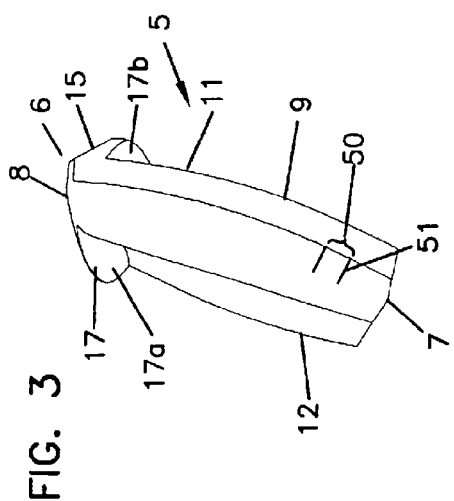
FIG. 3 is a perspective view of the working end of the surgical instrument of FIG. 1.

FIG. 2 is a side view of the surgical instrument 10 of FIG. 1 rotated 90 degrees around axis X—X and FIG. 3 is a perspective view of working head 5. As illustrated in FIG. 3, working head 5 includes a blade 9 having a first cutting edge 11 and a second cutting edge 12 extending substantially from leading end 6 to trailing end 7. However, blade 9 need not extend completely between leading end 6 to trailing end 7. Leading end 6 can also include a collecting element 15 having a tapered distal tip 16 facing away from the trailing end 7 and an opposing collecting surface 17 facing toward the trailing end 7. In the illustrated embodiment, collecting surface 17 includes a first collecting surface 17a and a second collecting surface 17b. Although preferred, collecting element 15 does not need to be present in an instrument of the invention.

FIG. 4 is a transverse cross-section view through line 4—4 of FIG. 1. As illustrated in this view, blade 9 has a serpentoid or "S" shaped configuration in cross-sectional view. Thus, blade 9 includes a first face 21 having a first concave surface 22 and a first convex surface 23. Blade 9 also includes a second face 25 having a second concave surface 26 and a second convex surface 27. In the illustrated embodiment, first cutting edge 11 faces in the same direction as first concave surface 22 and second cutting edge 12 faces in the same direction as second concave surface 26. Blade 9 of working head 5 has a height dimension H, a width dimension W that is less than height dimension H and a diagonal, or distraction height, dimension dH that is greater than height dimension H.

As best shown in FIG. 4, first collecting surface 17a extends from first face 21 over a portion of a region defined by first concave surface 22 at the leading end 6 of blade 9. A second collecting surface 17b extends from second face 25 over a portion of a region defined by second concave surface 26 also at the leading end 6 of blade 9. In preferred embodiments, cutting edge 11 protrudes radially beyond a peripheral edge 30 of collecting surface 17a. Likewise, in the illustrated embodiment, cutting edge 12 protrudes radially beyond a peripheral edge 31 of collecting surface 17b.

Figure 6:
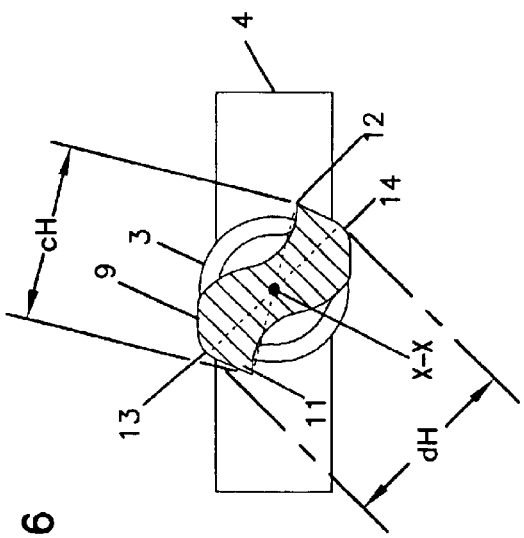
FIG. 6 is a transverse cross-section through line 6—6 of the surgical instrument of FIG. 1.
Figure 5:
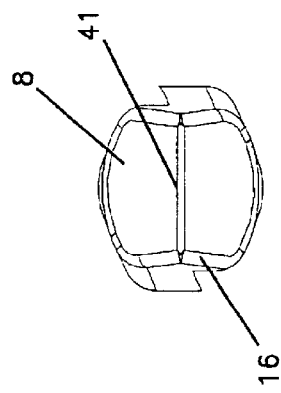
FIG. 5 is a distal end-on view of the surgical instrument of FIG. 1.

FIG. 5 is a distal end-on view of surgical instrument 10. In this view, it will be appreciated that the tapered distal tip 16 of collecting element 15 can include a distal apex 41 to facilitate passing instrument 10 between adjacent surfaces in a surgical field. FIG. 6 is a transverse cross-section view through line 6—6 of surgical instrument 10 illustrating blade 9 in relation to shaft 10. Blade 9 has a cutting height cH, measured between first cutting edge 11 and second cutting edge 12. Blade 9 also has a distraction height dH, measured between rounded distraction surfaces 13, 14. The cutting height cH is less than the distraction height dH.

As shown in FIG. 3, working head 5 can also include an indicator arrangement 50 such as markings 51 to indicate the depth of penetration of instrument 10 into a surgical site. The indicator arrangement 50 can include one or more markings that are incrementally spaced (e.g., 1 mm increments) that extend partially or fully around the working head.

Surgical instrument 10 provides for cutting, curetting and/or removing material cut or curetted from a surgical site. For exemplary purposes, use of surgical instrument 10 will be described with reference to an intervertebral disc space between adjacent vertebrae. However, it will be appreciated that other uses are within the scope of the invention. According to the present example, known methods can be used to provide exposure to the intervertebral disc space. An incision can be made into the vertebral annulus and the distal tip 16 inserted through the incision into the nucleus of the disc space. Alternatively, the annulus may have been previously herniated providing an access to the nucleus. It is also foreseen that the distal apex 41 of distal tip 16 can be forcefully inserted through an intact annulus into the nucleus without first making an incision into the annulus. The longitudinal axis of apex 41 can be passed through the annulus into the disc space in a plane substantially perpendicular to the long axis of the vertebral column.

It is foreseen that a blade 9 may have a diagonal dimension, or distraction height dH or cutting height dimension cH sufficient to distract the vertebrae adjacent the disc space. Instrument 10 can be inserted into the disc space with cutting height dimension cH oriented parallel to the end plates of the vertebrae. Once passed into the intervertebral space, the instrument 10 can be rotated in the direction of arrow 35 around longitudinal axis X—X by handle 4. When rotating in this direction cutting edges 11 and 12 are oriented to cut material (such as the nucleus or vertebral end plates) that is contacted by cutting edges 11 and 12 as instrument 10 is rotated. In addition, if distraction height dH is greater than the height of the disc space, during rotation, after cutting edges 11 and 12 contact the end plates of the vertebrae, blade 9 can also cause the end plates to distract or be forced apart from one another as the distraction height dH becomes oriented parallel to the long axis of the spinal column. When rotated in a direction opposite to that shown by arrow 35, the rounded distraction surfaces 13, 14 can still provide distraction of the vertebrae when the distraction height dH is oriented parallel to the long axis of the spinal column, but cutting edges 11 and 12 will not be oriented for cutting.

Thus, rotation of instrument 10 in one direction provides for cutting or curetting material. During rotation, the material cut can be stored along first and second concave surfaces 22 and 26. Specifically, the cut or curetted material collects along concave surfaces 22 and 26. If a collecting element 15 is present, removal of the cut material from the surgical site cam be facilitated by collecting surfaces 17a and 17b of collecting element 15. When surgical instrument 10 is removed from the surgical site, such as an intervertebral disc space, collecting element 15 facilitates removing the cut or curetted material from the surgical site.

From the foregoing detailed description and examples, it will be evident that modifications and variations can be made in the devices and methods of the invention without departing from the spirit or scope of the invention. Therefore, it is intended that all modifications and variations not departing from the spirit of the invention come within the scope of the claims appended hereto.

What is claimed is:

1. A surgical device for curetting an intervertebral disc between opposing first and second vertebrae, said surgical device comprising:
   a shaft having a proximal end and a distal end spaced apart along a longitudinal axis of said device;
   a blade extending from said distal end of said shaft, said blade having a leading end and a trailing end,
   said blade having a first concave surface facing a first direction and a first cutting edge and said blade having a second concave surface facing a second direction and a second cutting edge,
   said blade having a first cutting dimension, defined between said first cutting edge and said second cutting edge;
   distraction structure having a first non-cutting surface and a second non-cutting surface, the distraction structure having a second non-cutting dimension defined between said first non-cutting surface and said second non-cutting surface, said second non-cutting dimension being greater than said first cutting dimension.

2. The surgical device according to claim 1 further comprising a collecting element on said leading end of said blade, said collecting element overlying a portion of said first concave surface and said second concave surface at said leading end of said blade.

3. The surgical device according to claim 2 wherein said collecting element has a tapered surface facing away from said trailing end of said blade and a collecting surface facing toward said trailing end of said blade.

4. The surgical device according to claim 2 wherein a portion of a peripheral surface of said collecting element does not extend axially beyond a said first and second cutting edges.

5. The surgical device according to claim 1 wherein when said device is rotated in a first direction around said longitudinal axis said first and second cutting edges are oriented for cutting and when said device is rotated in a second direction around said longitudinal axis, opposite to said first direction said first and second cutting edges are not oriented for cutting.

6. The surgical device according to claim 1 wherein said first cutting edge is facing in a direction opposite said second cutting edge.

7. The surgical device according to claim 1 having a handle for rotating said instrument at said proximal end.

8. The surgical device according to claim 1 wherein the first and second non-cutting surfaces are rounded.

9. A curette comprising:
   a shaft having a proximal end and a distal end spaced apart along a longitudinal axis of said curette;
   a blade extending from said distal end of said shaft, said blade having a leading end and a trailing end;
   said blade having an undulating configuration such that, a first side of said blade has a first concave region and a first convex region and a second side of said blade has a second concave region and a second convex region;
   said first side having a first cutting edge and said second side having a second cutting edge;
   a collecting element at said leading end of said blade, said collecting element including a collecting surface oriented to face the trailing end of the blade.

10. The curette according to claim 9 wherein said first concave region and said second concave region face in opposite directions.

11. The curette according to claim 9 wherein said first concave region of said first side is adjacent said second convex region of said second side and said second concave region of said second side is adjacent said first concave region of said first side.

12. The curette according to claim 9 wherein when said curette is rotated in a first direction around said longitudinal axis said first and second cutting edges are oriented for cutting around said longitudinal axis and when said curette is rotated in a second direction around said longitudinal axis, opposite to said first direction, said first and second cutting edges are not oriented for cutting around said longitudinal axis.

13. The curette according to claim 12 wherein said first cutting edge is diametrically opposed to said second cutting edge.

14. The curette according to claim 13 wherein said collecting element has a tapered surface facing away from said distal end of said shaft.

15. The curette according to claim 9 wherein a portion of a peripheral surface of said collecting element does not extend beyond said first and second cutting edges.

16. The curette according to claim 9 having a handle for rotating said curette at said proximal end of said shaft.

17. A surgical device for curetting an intervertebral disc between opposing first and second vertebrae, said surgical device comprising:
   a shaft having a proximal end and a distal end;
   a blade positioned at the distal end of the shaft;
   said blade having first and second cutting edges and first and second distraction surfaces adjacent said first and second cutting edges; and
   said blade having a cutting height dimension extending between the first and second cutting edges and a non-cutting height dimension extending between the first and second distraction surfaces, wherein said non-cutting height dimension is greater than said cutting height dimension.

18. The surgical device according to claim 17 wherein the first and second distraction surfaces are rounded.

19. The surgical device according to claim 17 wherein the first and second distraction surfaces are shaped such when the surfaces contact the first and second vertebrae, the first and second vertebrae are force apart without curetting any portion of the first and second vertebrae.

20. A surgical device for curetting an intervertebral disc between opposing first and second vertebrae, said surgical device comprising:
   a shaft having a proximal end and a distal end;
   a blade positioned at the distal end of the shaft;
   said blade having first and second cutting edges separated by a first distance and first and second non-cutting surfaces separated by a second distance, said non-cutting surfaces being adjacent to said first and second cutting edges; and
   said second distance being larger than said first distance.

21. The surgical device according to claim 20 wherein the first and second non-cutting surfaces are rounded.

22. A surgical device for curetting an intervertebral disc between opposing first and second vertebrae, said surgical device comprising:

a shaft having a proximal end and a distal end, the shaft defining an axis of rotation;

a blade positioned at the distal end of the shaft with the axis of rotation of the shaft passing through the blade;

the blade having first and second rounded distraction surfaces positioned at opposite sides of the of the axis of rotation, the distraction surfaces facing outwardly from the axis of rotation and being separated by a distraction dimension that passes through the axis of rotation; and the blade having first and second cutting edges positioned at opposite sides of the axis of rotation, the first and second cutting edges being separated by a cutting dimension that passes through the axis of rotation, the cutting dimension being less than the distraction dimension.

* * * * *